(12) United States Patent
Grune et al.

(10) Patent No.: US 9,913,787 B2
(45) Date of Patent: *Mar. 13, 2018

(54) GLYCERINE BASED JELLY COMPOSITIONS

(71) Applicants: Guerry L. Grune, Virginia Beach, VA (US); William Wingfield, Richmond, VA (US); Martin E Oehlbeck, Cohocton, NY (US)

(72) Inventors: Guerry L. Grune, Virginia Beach, VA (US); William Wingfield, Richmond, VA (US); Martin E Oehlbeck, Cohocton, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/953,568

(22) Filed: Nov. 30, 2015

(65) Prior Publication Data

US 2016/0338923 A1    Nov. 24, 2016

Related U.S. Application Data

(63) Continuation of application No. 14/714,875, filed on May 18, 2015, now abandoned.

(51) Int. Cl.
| | | |
|---|---|---|
| *A61K 8/34* | (2006.01) |
| *A61Q 17/04* | (2006.01) |
| *A61K 8/27* | (2006.01) |
| *A61K 8/55* | (2006.01) |
| *A61K 8/97* | (2017.01) |
| *A61K 8/98* | (2006.01) |
| *A61K 8/60* | (2006.01) |
| *A61K 8/67* | (2006.01) |

(52) U.S. Cl.
CPC ............ *A61K 8/345* (2013.01); *A61K 8/27* (2013.01); *A61K 8/553* (2013.01); *A61K 8/602* (2013.01); *A61K 8/678* (2013.01); *A61K 8/97* (2013.01); *A61K 8/988* (2013.01); *A61Q 17/04* (2013.01); *A61K 2800/30* (2013.01); *A61K 2800/49* (2013.01); *A61K 2800/522* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 5,679,361 | A | 10/1997 | Pradier et al. |
| 5,976,560 | A | 11/1999 | Han et al. |
| 6,673,863 | B2 | 1/2004 | Travkina et al. |
| 7,393,548 | B2 | 7/2008 | Friedman |
| 2002/0128163 | A1 | 9/2002 | Lambino et al. |
| 2004/0067244 | A1 | 4/2004 | Friedman |
| 2008/0069779 | A1 | 3/2008 | Tamarkin et al. |
| 2008/0233060 | A1 | 9/2008 | Grune |
| 2009/0298801 | A1 | 12/2009 | Galderma et al. |
| 2011/0064832 | A1* | 3/2011 | Burke-Colvin ........ A61K 8/585 424/727 |
| 2012/0328538 | A1 | 12/2012 | Grune et al. |

FOREIGN PATENT DOCUMENTS

| | | |
|---|---|---|
| CA | 1244350 | 11/1988 |
| CA | 2130450 | 9/1993 |
| CA | 2161285 | 4/1996 |
| CA | 2821513 | 6/2013 |
| EP | 2509632 A2 | 10/2012 |

* cited by examiner

*Primary Examiner* — Robert A Wax
*Assistant Examiner* — Randeep Singh
(74) *Attorney, Agent, or Firm* — ePatentManager.com; Garry L. Grune

(57) ABSTRACT

The disclosure describes a replacement for petroleum jelly as a base for products which is suitable for most any application for which petroleum jelly can be used. The jelly is a glycerine based composition comprising; vegetable derived glycerine and an emulsifier. The emulsifier can be any known and/or commercially available glucoside containing substance. Other suitable emulsifiers together with glycerine and essential or vegetable based oils with or without inorganic fillers may be added to impart desirable mechanical and physio-chemical properties. In addition, temperature stabilizers and stiffening agents such as waxes and other inorganic fillers including silica and clays may also be added during manufacture. The composition includes glycerine preferably present in the range of 50-95 weight %.

12 Claims, No Drawings

GLYCERINE BASED JELLY COMPOSITIONS

PRIORITY STATEMENT

This application is a continuation of and claims priority to U.S. nonprovisional application Ser. No. 14/714,875, filed May 18, 2015, entitled "Glycerine Based Jelly Compositions", which is continuation of Ser. No. 14/529,804, filed Oct. 31, 2014, entitled "Glycerine Based Jelly Compositions", which is a continuation of Ser. No. 14/230,162, filed Mar. 31, 2014, entitled "Glycerine Based Jelly Compositions", which is a continuation of Ser. No. 14/022,461, filed Sep. 10, 2013, which is a continuation of Non-Provisional application Ser. No. 13/515,205 filed Jun. 11, 2012, and granted on Oct. 15, 2013 as U.S. Pat. No. 8,557,264, which was entered as a National Stage filing application under 35 USC 371 from PCT/US 2010/059634 filed Dec. 9, 2010, both entitled "Glycerine Based Jelly Compositions", which is a PCT filing of and claims priority under 35 USC 119 from Provisional Application No. 61/ 285,298 filed Dec. 10, 2009 entitled "Glycerine Based Jelly Compositions Incorporating Additives" and Provisional Application No. 61/345,383 filed May 17, 2010 entitled "Glycerine Based Jelly Compositions Incorporating Additives"

The following patent and patent applications are also hereby incorporated by reference and where appropriate also provide priority under 35 USC 120 regarding any necessary SPF formulations to be used together with the jelly compositions of the present disclosure;

U.S Pat. No. 6,866,841 entitled "Non-endocrine disrupting cytoprotective UV radiation resistant substance"

PCT Application No. US2007/005672 filed May 5, 2007 entitled "Sunscreen Compositions"

U.S. application Ser. No. 11/807,192 filed May 25, 2007 entitled "High SPF Transparent or Transluscent Naturally Derived, Cytoprotective, UV Resistant Compostions"

U.S. application Ser. No. 11/805,710 filed Aug. 18, 2007 entitled "Non-Endocrine Disrupting Cytoprotective, UV Radiation Resistant Sunblock Compositions"

U.S application Ser. No. 12/074,906, filed Mar. 7, 2008 entitled "SPF Compositions"

U.S application Ser. No. 12/074,907 filed Mar. 7, 2008 entitled "Sunblock Formulations"

U.S. patent application Ser. No. 12/077,369 field Mar. 19, 2009 entitled" High SPF Transparent or Translucent, Cytoprptective, Biodegradable, "UV Radiation Resistant Compositions"

U.S. Application No. 61/281,695 entitled "All Natural SPF Boosting Zinc Oxide Complex" filed Nov. 20, 2009

U.S. Application No. 61/281,694 entitled "Broad Spectrum UVA Stable Non-Toxic, Zinc Oxide Complex" filed Nov. 20, 2009

FIELD OF THE INVENTION

The present invention relates to a petroleum-free jelly and a field of products suitable for application to the skin and, in particular, to a replacement for petroleum jelly as a base for many existing products. Additional products that are being emphasized in this continuation application include food grease products.

BACKGROUND OF THE INVENTION

Products which are applied to the skin such as cosmetics or lotions often use petroleum jelly as a base. Petroleum jelly is inexpensive, abundant, and can be smoothly applied to the skin. However, petroleum jelly has a number of disadvantages. In particular, petroleum jelly is a petroleum based product which may cause dermatitis on the skin and can be toxic. Also of rather recent importance to more people is the fact that they consider petroleum based products objectionable.

In recent years, more skin care products have become available which utilize natural oils and ingredients in place of petroleum jelly. Examples of such products are disclosed in Canadian Patent 1,244,350 issued Nov. 8, 1988 for a skin care and shaving composition; Canadian patent application 2,161,285 published Apr. 26, 1996 disclosing a cosmetic composition; and Canadian Patent Application 2,130,450 published Sep. 2, 1993 disclosing insect repellent. Each of these references is directed towards products adapted for application to the skin and incorporate natural oils. However, these natural oils are not suitable as a general replacement for petroleum jelly but rather are disclosed in specific mixtures in products applied to skin. These products also do not overcome the disadvantages of a petroleum jelly base such as a low melting temperature or are based on hydrogenated oils which congeal at room temperature into a jelly like substance but which when heated or when reaching above average room temperatures may result in reduced shelf life as well as objectionable feel and odor.

U.S. Pat. No. 5,679,361 issued Oct. 21, 1997 and discloses a solid or pasty make-up composition. The composition is comprised of a fatty phase and a pulverulent phase. The fatty phase is 20-70% by weight of the total weight of the composition. The pulverulent phase is a light powder which is present in an amount of 5-30% by weight of the total composition. This patent is directed towards a process for preparing the make-up composition. In this process, the powder is used for the processing and pressing of the composition and reacts with the other ingredients in the make-up to form a final product. The fatty phase may incorporate a vegetable oil. This composition provides a product with an improved feel on application but it does not provide for a product with a raised melting point or a product which will not separate out on heating.

There therefore is a need for a general replacement for petroleum jelly as a base for products for application to skin which is non-petroleum based as well as a jelly which is primarily or completely oil-free and also non-toxic but maintains the physical and aesthetic attributes of petroleum jelly. Here, the definition of a toxic substance is any substance which kills cells on contact and/or any endocrine disrupting substance as tested using the LUMI-CELL® techniques perfected by Dr. George Clark, director of Xenobiotics in Durham, N.C. It is also advantageous and a subject of the present disclosure to provide an oil-free, substantially oil-free, or even oil containing jelly that meets all Ecocert® certifications and approvals.

There is also a need for a replacement for petroleum jelly suitable for use in a variety of products, including lubrication enhancers, anti-corrosive agents, as well as general purpose manufacturing and household products such that providing a jelly-like petroleum free substance creates an improved or enhanced product or handling of the product. Further, there is a need for a replacement for petroleum jelly, the replacement being derived from natural ingredients such as plant products that does not require vegetable oils, especially hydrogenated vegetable oils and is derived from vegetable based glycerine and one or more vegetable derived emulsifiers.

SUMMARY OF THE INVENTION

The present disclosure describes a replacement for petroleum jelly as a base for products suitable for essentially any application for which petroleum jelly can be used. The present application describes a jelly primarily comprised of vegetable derived glycerine with one or more a vegetable derived glucoside-based emulsifier. Other suitable emulsifiers together with glycerine and essential or vegetable based oils with or without inorganic fillers may also be added to the jelly to impart fragrance, color, UVA and UVB sun protection factor, immuno-enhancing aromatherapeutics, as well as free radical scavenging constituents. In addition, temperature stabilizers and stiffening agents such as waxes and other inorganic fillers including silica and clays are to be added as required. The glycerine is preferably present in the range of 50-95% and more preferably 90% and most preferably 92.5% with 7.5% of an emulsifier such as a polyglucoside and in particular cetearyl glucoside. Other ingredients which may be added include vitamins and provitamins, carotenoids, aloe vera gel or aloe vera juice.

It is therefore an object of the present invention to overcome the disadvantages described in the prior art and to provide a replacement for petroleum jelly as the base in products suitable for application to the skin, where the replacement jelly is predominantly comprised of glycerine.

It is also an object of the present invention to provide an alternative to petroleum jelly composition which is oil free and also may have a higher melting point than petroleum jelly.

It is a further object of the present invention to provide a composition which incorporates essential (primarily steam processed) oils, natural waxes, inorganic fillers, carotenoids, anti-oxidants, free radical scavengers, and Ecocert® approved emulsifiers and emollients including aloe vera gel and juice.

Thus, therefore, is provided an oil-free vegetable derived glycerine base for a product suitable for application to skin or a lubricant composition, said base comprising vegetable oil and silica.

Use of the base oil-free jelly with active sunscreen and sunblocking agents is also an embodiment of the present disclosure.

Yet a further embodiment is related to the fact that it has been found that some of the glycerine/emulsifier combinations that have been formulated without any additives have a tendency to provide a "sticky" feel after application to the skin. There are several combinations of the jelly which have been developed which ameliorate or eliminate this sticky feel. Specifically, the use of higher speed mixing allows for air to become incorporated into the formulations and causes some "foaming" of the composition during heating, which, when cooled provides a lower density, air or gas-filled product. This composition reduces and/or eliminates the stickiness associated with products which do not incorporate air. The air or inert gases could be added by forcing the gas into the mixture while slowly agitating the composition, thereby controlling the amount of gas added, resulting in a similar "foamed" composition.

Yet another embodiment that also involves reducing the sticky feel of the glycerine/emulsifier composition of the present application is to incorporate various additives including starches from various plants such as arrowroot and corn, inorganic salts including calcium, magnesium, zinc, titanium and other inorganic metals and metal oxides, clays, including igneous, sedimentary, and metamorphic types as well as inorganic polymers. All inorganic particles may be added in either a micronized or even nanosized particle form (as powders or otherwise) to the glycerine/emulsifier composition in various weight percent ranges to allow for proper incorporation of these additives. Proper incorporation, in this instant, refers to the making of a useful, less sticky jelly or gelled composition that provides additional chemical and/or physic-chemical and/or physic-mechanical attributes. The use of arrowroot and/or talc (up to 10 percent by weight of the total composition) in combination with the 85 weight percent glycerine and 15 weight percent cetearyl glucoside compound, resulted in a foamed white appearing solid jelled substance with greatly reduced stickiness.

An additional embodiment includes use of additional inorganic and organic additives in the glycerine/emulsifier composition described in the present application allows for imparting most other required properties for a gel including; flame retardance, UV resistance, physio-mechanical strength and better bonding characteristics useful for any materials of construction, ointments for medicinal and other purposes, lubrication for both biological and mechanical needs, and as a carrier for food and/or pharmaceutical grade products.

DETAILED DESCRIPTION OF THE INVENTION

The present disclosure describes a replacement for petroleum jelly as a base for products suitable for most any application for which petroleum jelly can be used. It is comprised primarily of vegetable derived glycerine and a vegetable derived glucoside-based emulsifier. Other suitable emulsifiers together with glycerine and essential or vegetable based oils with or without inorganic fillers may also be added to the jelly to impart fragrance, color, UVA and UVB sun protection factor, immuno-enhancing aromatherapeutics, as well as free radical scavenging constituents. In addition, temperature stabilizers and stiffening agents such as waxes and other inorganic fillers including silica and clays may be added as required. The glycerine is preferably present in the range of 50-95% and most preferably 90%. Other ingredients which may be added include vitamins and provitamins, carotenoids, aloe vera gel or aloe vera juice.

Additional ingredients may be added to the present invention to improve its suitability as a base for a skin care product. Other preferred ingredients which may optionally be added to the present disclosure include suitable vegetable oils including all vegetable oils but not including hydrogenated vegetables oils. These vegetable oils may be selected from, but are not limited to, canola oil, sunflower oil, soybean oil, corn oil, cottonseed oil, olive oil, wheat germ oil, borage oil, evening primrose oil, black currant oil, linseed oil, peanut oil, raspberry seed oil, carrot oil, avocado oil, and safflower oil.

The use of silica present in the composition of the present disclosure is in a powder form and may be silica powder or silicone dioxide powder. In particular, untreated fumed silica powder may also be used. Preferably, the average particle length is 0.2 to 0.3 microns. The primary use of the silica is to impart stiffness and thermal stability.

Vitamin E may be included in the oil-free glycerine and emulsifier base of the present disclosure. It is preferably present in an amount in the range of 0 to 1% of the total weight of the composition. More preferably, it is present in an amount of approximately 0.1% by weight. Preferably, tocopherols and its derivatives are used and, more preferably, dl-alpha-tocopherol.

Starch is a further optional ingredient in the composition of the present invention. It is preferably present in an amount in the range of 0 to 15% by weight of the total composition. Preferably, corn starch or arrowroot powder is used and also impart stability to the oil-free jelly.

Sunscreens are preferably present in an amount in the range of 0 to 15% by weight of the total composition. The preferred amount is approximately 7% by weight. Sunscreens include those as defined in the FDA Regulatory Book 21 CFR Part 352, 700 and 740 dated Apr. 5, 1994 . Any recognized sunscreen may be used and preferred sunscreens include octyl methoxycinnamate, octyl salicylate, titanium dioxide, zinc oxide, etc. The goal of the present disclosure is to incorporate non-endocrine disrupting active sunblocking agents.

The industry currently formulates using "pre-fabricated" dispersions in that the dispersions are purchased from a secondary source and mixed in with existing lotions, pastes, cremes, etc. This technique is acceptable if the zinc oxide dispersion is provided in a non-endocrine disrupting suspension.

In addition, the need for an acceptable emollient that reduces the negative affects associated with abrasive inorganics and that also includes the benefit of providing cytoprotection and healing of the skin is necessary. Allowing for the reduction of irritation or sensitization of the skin suggests that "cold-pressed" Aloe is a useful and necessary ingredient for such a formulation.

It has also been determined that it is quite difficult, if not impossible, for current dispersion systems for micronized $TiO_2$, $ZnO$, $SiO_2$ and the like to be endocrine-disruptor free. As discussed below, the endocrine disrupters in the LUMI-CELL® test technique have been found to kill cells. Therefore, in essence, using one of several definitions of toxicity—adverse effects occurring as a result of repeated daily dosing of a chemical or exposure to the chemical, for part of an organism's lifespan—the dispersions themselves are toxic. The present disclosure includes the possible use of aloe, not only as an emollient, but also as a very effective dispersing agent for the inorganic micronized (and larger) sunblock active agents. High speed shearing (accomplished in a Waring blender for example), followed by high speed mixing (up to 2000 rpm with an IKA mechanical stirrer—Wilmington, N.C. for example) provides a consistent, usable, and easily blendable inorganic/organic dispersion free of any known toxic substances (if the aloe source and inorganic particle source is well documented and controlled). The dispersion is essential in providing sufficient homogeneity and SPF values with any associated non-active cream, lotion, gel, spray, etc. that is used to provide a formulation consistent with the basis of the present disclosure.

To provide a proper SPF value, it is also necessary to enhance or boost the SPF number using boosting agents. These also may not be endocrine disrupters or toxic (cell-killing) or both. It is likely that many natural oils and perhaps derivatives of other natural occurring substances (such as essential oils of safflower, sunflower, rice bran, eucalyptus, rosemary, peru balsam, olibanum, orange, almond, sesame, ylang ylang, jojoba, or coconut) that can provide dispersion capabilities to enhance SPF may be determined to be free of endocrine disrupting capabilities. It has also become known that to increase SPF values for both in vivo and in vitro testing, film forming properties are important. The following film forming agents may also be used in the present disclosure: wheat protein extract, silk protein, galactoarabian, marine collagen, pea extract, purcellin oil, preen oil, as well as wild mango butter and kikui nut oil, etc.

Bentonite can be used to boost SPF values as well as provide stability for the jelly of the present disclosure. Colloidal Bentonite contains the active constituent montmorillonite super-refined with demineralized water as a vehicle. The liquid bentonite was the first of its kind to be processed removing the dirt, mica and impurities leaving the active ingredient Montmorillonite in a colloidal suspension. The Montmorillonite molecule has a shape similar to a business card with the wide surfaces negative and the edges of the card positively charged. This allows it to have many times more negative than positive charges. In addition, the very minuteness of the particles of Montmorillonite provides a large surface area in proportion to the volume used, thus enabling it to pick up many times its own weight in positively charged particles. To obtain maximum effectiveness in the human body, it must be put in a liquid colloidal-gel state. When a volcano erupts, there is often a fine steam or mist released which contains a substance known as volcanic ash. Bentonite is a volcanic ash. As it contains many minerals (24 to 33), it serves to mineralize the soil. Bentonite clay can be mined from veins, which are two to three feet wide and deep, but many yards long. Natives on every continent have used volcanic ash for centuries both internally and externally. The value of montmorillonite (the active ingredient in bentonite) lies in its ability to adsorb (not absorb) many times its own weight and volume in an aqueous medium. It has a predominantly negative charge that is capable of attracting many kinds of positively charged particles. Its negative charge enables it to pick up positively charged, toxic material from the alimentary canal to be expelled in the feces. The adsorption is a rapid process and can quickly neutralize allergens before they attach themselves to blood cells, thus preventing allergic reaction.

Aloe Vera gel serves numerous purposes in the present disclosure, including acting as a dispersant, as an emollient, boosting the SPF value, and improving aesthetics, and is believed by many to have healthful benefits. For medicinal purposes, aloe vera is most commonly used externally to treat various skin conditions, and burns. Not only does it soothe the skin, ease pain and reduce inflammation, studies have been done to show that using aloe as a topical treatment for burns will help speed up the healing recovery process. Many cosmetic companies are now adding this plant to products including makeup, soaps, sunscreens, shampoos and lotions, as well as any product that is created to soothe, protect and moisturize the skin. This is due partially to the fact that aloe extract is full of vitamins, nutrients and minerals.

The compositions of this disclosure may, include one or more of a select group of anionic emulsifiers. In particular, salts of certain fatty acids are useful in the formulations of this disclosure, preferably salts of saturated fatty acids and/or salts of straight-chain fatty acids. Alkali metal salts, alkali earth metal salts and amine salts are more preferable for use in the compositions of this disclosure. For example, stearic acid and its salts are useful as emulsifiers in the compositions of this disclosure, while the use of isostearate salts tends to produce a composition which is not very efficient in the use of sunscreen. Likewise, oleate salts are not useful as they are unsaturated and do not result in efficient sunscreen compositions. Sodium borate is an example of a preferred salt. The family of glucoside based emulsifiers, when mixed with glycerine, provides a homogenous jelly with an appearance and physical properties very close to that of petroleum jelly.

The emulsifiers should be present in the compositions of this disclosure in an amount from about 0.01 to about 10%, more preferably 0.1 to about 7% and most preferably from about 0.5 to about 7.5%. There may be additional emulsifiers present in the compositions of this disclosure, including but not limited to a combination of cetearyl glucoside and cetearyl alcohol. However, at least one emulsifier should be present in order to achieve the products of this disclosure. The fatty acid salt emulsifiers may be added to the composition as the salts, or the salt may be formed in situ.

Phosphatidyl-choline (PC), a phospholipid also known as lecithin and PhosChol, can also be used as a natural dispersant and/or emulsifier. It is the major component of a phosphatide fraction which may be isolated from either egg yolk or soy beans from which it is mechanically or chemically extracted using hexane. It is commercially available in high purity as a food supplement and for medical uses. PC is regarded as a well tolerated and non-toxic surfactant. It is approved by the United States Food and Drug Administration for human consumption with the status "Generally Recognized as Safe". Lecithin is an integral part of cell membranes, and can be totally metabolized, so it is virtually non-toxic to humans. Other emulsifiers can only be excreted via the kidneys. Some commercially available PC products are Phospholipon 90G® and Phospholipon 85G®, distributed by the American Lecithin Company of Oxford CT. PC can be dispersed into an oil, glycerin, aloe vera, or otherwise suitable solvent before being added into the present formulations of the present disclosure as an emulsifier or dispersant.

A liposome is a spherical vesicle with a membrane composed of a phospholipid bilayer used to deliver drugs or genetic material into a cell. Liposomes can be composed of naturally-derived phospholipids with mixed lipid chains (like egg phosphatidyl-ethanolamine), or of pure components like DOPE (dioleolylphosphatidylethanolamine). The lipid bilayer can fuse with other bilayers (e.g., the cell membrane), thus delivering the liposome contents. By making liposomes in a solution of DNA or drugs, (which would normally be unable to diffuse through the membrane), they can be (indiscriminately) delivered past the lipid bilayer.

Liposomes can be created by sonicating phospholipids in water. Low shear rates create multilamellar liposomes, which have many layers like an onion. Continued high-shear sonication tends to form smaller unilamellar liposomes. In this technique, the liposome contents are the same as the contents of the aqueous phase. Liposomes can be used as emulsifiers in the same manner as the phospholipids discussed above.

Humectants can form an important part of the present disclosure. The main purpose of any cream is to keep the skin moist. Many conventional creams form a suffocating film on the skin to prevent moisture loss. Even as natural humectant, glycerin, actually attracts water from the air and surrounding tissue. It keeps the skin moist as long as there is sufficient moisture in the air. In a dry climate it actually draws moisture from the skin. Collagen, elastin, panthenol (pro-vitamin B5) and keratin enjoy some popularity as humectants. Another example is Pepha®-Nutrix, a product of Pentapharm Ltd of Basel, Switzerland.

Natural phospholipids, or lecithin, are also an excellent humectant. An important benefit of phospholipids is that they are hygroscopic (attract water from the surrounding air) and hold water where an increased level of hydration is needed. Therefore, phospholipids increase the hydration levels of the skin without being occlusive (forming a film to prevent water loss, and preventing normal cellular function).

A carrier oil is useful in the compositions of this disclosure. There are a range of different carrier oils each with their own individual properties and suitability towards different treatments in aromatherapy. The carrier oil may be selected from the group of essential oils or other known non-endocrine disrupter esters. Other carriers include castor oil, avocado oil, broccoli seed oil, keratin, and micronized or colloidal bentonite.

Preferably, the carrier oil which is more preferably an essential oil, should be present in the composition in an amount of between about 0.1% and about 10%. More preferably, it should be present in the amount of between about 1% and about 5%. Most preferably, it should be present in the amount of between about 2% and about 4%. All essential oils are non-endocrine disrupting. Examples of essential oils include oils of jojoba, rice bran, sesame, safflower, almond, sweet almond, eucalyptus, sunflower, peru balsam, rosemary, olibanum, orange, sunflower, ylang ylang, apricot kernel, avocado, borage, cocoa butter, evening primrose, grapeseed, hazelnut, kukui, macadamia nut, olive, peanut, pecan, rose hip, bergamot, jasmine, neroli, patchouli, petitgrain, rose, vetiver, chamomile, mandarin, lavender, grapefruit, cypress, bay laurel, frankincense, clary sage, ginger, helichrysum, lemon, sandalwood, basil, black pepper, peppermint, geranium, wintergreen, thyme, tea tree, tangerine, spearmint, common sage, rosewood, pine, patchouli, oregano, nutmeg, myrrh, melaleuca, marjoram, manuka, lemon grass, lavender, juniper, ginger, cumin, clove, camphor, bay leaf, anise, allspice, and hyssop.

A number of the above mentioned essential oils, including jojoba and avocado, can be utilized in the present formulations as emollients. A number of the above mentioned essential oils, including rosemary and frankincense, can be also be utilized for their aromatherapeutic properties, thus being incorporated as a fragrance.

A third element may also be present in the compositions of this disclosure is an inorganic sunscreen compound, such as titanium dioxide, zinc oxide or combinations thereof. Possible other inorganics include the use of fused or fumed silica or even silicon dioxide. Preferably, titanium dioxide, zinc oxide, silica, silicon dioxide, or cosmetic microspheres should be used having a primary particle size of less than about 300 nm in diameter. It should be present in the composition in the amount of from about 2% to about 25%. More preferably, it should be present in the amount of from about 2% to about 15%. The inorganic sunscreen compound should be oil or water dispersible, and may be present with or without surface coating.

The ratio of titanium dioxide or zinc oxide to the weight of the carrier oil and the emollient combined should be from about 0.0:1 to about 1:1 . More preferably, the ratio should be between about 0.25:1 and 2:3, and most preferably 0.33:1.

In the case where salts of fatty acids are used care should be taken to keep the pH of the compositions of this disclosure at a level above about 5, more preferably, above about 5.5. Maintaining the pH at this level will ensure that these anionic emulsifiers remain in the salt form, which is important in retaining the stability and efficacy of the composition.

Additionally, the usual elements of a modern sunscreen emulsion system may be necessary such as a polymeric thickener/stabilizer, one or more additional emollient oils, microbial preservatives, waterproofing agents, antioxidants, fragrance, humectant, and of course the water vehicle may all be utilized using careful selection or restraint based on the constraints of providing a non-endocrine disrupting immuno-enhancing composition.

The base formulation of this disclosure may also be used as carrier compositions for active topical agents having dermatological effects, including depigmentation agents, anti-aging ingredients, anti-fungal agents, anti-microbial agents, insect repellents and the like. For example, depigmentation agents can include magnesium ascorbyl phosphate or hydroquinone but only used in the final composition if these agents are shown not to be endocrine disrupters. Anti-aging agents can include retinoid compounds and alpha-hydroxy acids again only if these agents are shown not to be endocrine disrupters. Anti-fungal agents that can be included in the compositions of this disclosure include azole compounds including ketoconazole and the like again only if these agents are shown not to be endocrine disrupters. Anti-microbial agents include triclosan, an agent regarding cytotoxicity or endocrine disruption function. Insect repellant fragrances can be included in the compositions of this disclosure again only if these agents are shown not to be endocrine disrupters. Other products known to those of ordinary skill in the art may be delivered to the skin using the compositions of this disclosure.

The compositions of this disclosure would then have minimally a multi-action capability, as they would contain both sunscreen agents and other actives for protecting, treating, and enhancing the immuno-responsive nature of the skin.

The compositions of this disclosure can be incorporated into various cosmetic and personal care products such as hand and body lotions, oils, ointments, lip balm products, facial cosmetics and the like.

One of the major challenges in providing the composition of the present disclosure is to provide a non-toxic, non-endocrine disrupting, immuno-enhancing high (15 or greater) SPF formulation that can be readily achieved in a manufacturing environment for a reasonable cost. The use of aloe as both an emollient and a surfactant/dispersion agent together with either micronized ZnO, titanium dioxide, silicon dioxide, fluoropolymers, silica, etc. (inorganic or acceptable organic sun-block agents) in the manner outlined above is unique and novel. The addition of SPF boosting agents that are neither toxic nor endocrine disrupters is also unique to this disclosure and has heretofore not been seriously considered or explored.

The well known and commercially available "SPF boosters" have almost without exception proven to be toxic or endocrine disrupters or both and the present disclosure includes a scientifically accepted and peer reviewed method to assure the use of only SPF boosters that are neither toxic nor endocrine disrupters. The use of phospholipids or liposomes described above may also provided the needed oil-water dispersion and thus boost SPF.

The use of green tea extract may be effective in reducing sunburn. Green tea is a powerful antioxidant that neutralizes free radicals from UV radiation and helps protect skin cells by its photoprotective effect on human skin and its polyphenolic antioxidant contents. Green tea protection works in the cell after exposure to ultraviolet rays. Studies suggest it causes abnormal cells to kill themselves, a type of programmed cell suicide that prevents the development of abnormal growths. Green tea inhibits UVB-induced erythema response in the skin (redness reaction). At the same time it supports the production of melanin, the skin's own natural sunburn protection. Thus green tea helps reduce the risk of sunburn and boosts SPF.

Tocopherol, or Vitamin E oil, is a fat-soluble vitamin in eight forms that is an important antioxidant. Vitamin E is often used in skin creams and lotions because it is believed to play a role in encouraging skin healing and reducing scarring after injuries such as burns. Natural vitamin E exists in eight different forms or isomers, four tocopherols and four tocotrienols. All isomers have a chromanol ring, with a hydroxyl group which can donate a hydrogen atom to reduce free radicals and a hydrophobic side chain which allows for penetration into biological membranes. There is an alpha, beta, gamma and delta form of both the tocopherols and tocotrienols, determined by the number of methyl groups on the chromanol ring. Each form has its own biological activity, the measure of potency or functional use in the body. For the present disclosure, the most stable forms of vitamin E are desired.

Rosehip, also called the rose haw, is the pomaceous fruit of the rose plant and a powerful antioxidant. It is typically red to orange but may be dark purple to black in some species. Particularly high in vitamin C, with about 1700-2000 mg per 100 g in the dried product, it is one of the richest plant sources of the vitamin. It also contains vitamins A, D and E, and antioxidant flavonoids. Rosehip can be used as an emollient in the present disclosure. The use of vitamin C (ascorbic acid or other available forms of Vitamin C) in sunscreen or sunblock formulations should be in a stabilized form such as Magnesium ascorbyl phosphate. For the present disclosure and associated formulations, the most stable form of Vitamin C can be incorporated.

Keratins may also provide an SPF boost to the present compositions. Keratins are a family of fibrous structural proteins; tough and insoluble, they form the hard but non-mineralized structures found in reptiles, birds and mammals. They are rivaled in biological toughness only by chitin, a cellulose-like polymer of glucosamine and the main constituent of the exoskeletons of arthropods. The properties which make structural proteins like keratins useful depend on their supermolecular aggregation. These depend on the properties of the individual polypeptide strands, which depend in turn on their amino acid composition and sequence. The α-helix and β-sheet motifs, and disulfide bridges, are crucial to the conformations of globular, functional proteins like enzymes, many of which operate semi-independently, but they take on a completely dominant role in the architecture and aggregation of keratins. Keratins contain a high proportion of the smallest of the 20 amino acids, glycine, whose "side group" is a single hydrogen atom; also the next smallest, alanine, with a small and uncharged methyl group. In the case of β-sheets, this allows sterically-unhindered hydrogen bonding between the amino and carboxyl groups of peptide bonds on adjacent protein chains, facilitating their close alignment and strong binding. Fibrous keratin molecules can twist around each other to form helical intermediate filaments. In addition the family of carotenoids (as anti-oxidants) may also be added to the composition of the present disclosure.

Sucrose stearate is usually a white or light brown block or powder, with little or no smell and no taste. It is an exceptionally mild emulsifier derived from sugar and coconut or palm oil. Sucrose stearate is made by combining sugar with Stearic Acid. Cane sugar is a sweetening agent and food which can act as a preservative and antioxidant, and stearic acid is a natural fatty acid derived from coconut or palm oil. Because it is made from vegetable sources it is completely biodegradable. One commercially available form of sucrose stearate is Crodesta® F-160, manufactured by Croda of Yorkshire, England.

Lanolin is a thick natural moisturizer to soothe and protect skin. It is derived primarily from the oil glands in sheep's wool, also known as wool oil, wool wax, wool fat, or wool grease. Wool fat is a mixture of many different chemical compounds, including cholesterol and the esters derived from 'fatty' acids containing 18 to 26 carbon atoms. Lanolin is used in many skin formulas to prevent possible irritation from other oils. It functions as a salve and an emollient by sealing in your body's moisture, and is a natural water repellant. Lanolin forms an emulsion with water that's easily absorbed by the skin, softening it and preventing it from frying and cracking It is used for dry skin, sunburn, and windburn, and may also boost SPF.

A number of oils are used in commercial sunblocks as SPF boosters. Such oils may be effective at boosting SPF on their own in some cases, or in combination with other oils in other cases.

Among these oils are sunflower oil, safflower oil, almond oil, rice bran oil, eucalyptus oil, sesame oil, orange oil, jojoba oil, rosemary oil, peru balsam oil, grape seed oil, pomegranate seed oil, raspberry seed oil etc. Certain waxes may also have a positive SPF effect, including beeswax, orange wax, synthetic waxes and the like.

Beeswax is a product from a beehive. Beeswax is secreted by honeybees of a certain age in the form of thin scales. It is a tough wax formed from a mixture of several compounds; its main components are palmitate, palmitoleate, hydroxypalmitate and oleate esters of long-chain (30-32 carbons) aliphatic alcohols, with the ratio of triacontanylpalmitate $CH_3(CH_2)_{29}O-CO-(CH_2)_{14}CH_3$ to cerotic acid $CH_3(CH_2)_{24}COOH$, the two principal components, in a ratio of 6:1. Beeswax is used commercially to make fine candles, cosmetics and pharmaceuticals including bone wax (cosmetics and pharmaceuticals account for 60% of total consumption), in polishing materials (particularly shoe polish), as a component of modeling waxes, and in a variety of other products. For the present disclosure, the use of Hydroxyoctacosanyl hydroxystearate can not be used as a beeswax substitute as a consistency regulator and emulsion stabilizer. Japan wax is another substitute that may not be used. Beeswax's primary use in the present disclosure is to increase the water-resistant capabilities of the composition. The beeswax can also be impregnated with sun-block materials (micronized zinc oxide and titanium dioxide, etc.) in order to prevent these materials from being easily washed away during use.

Skin care products do not last forever. Just like food, all natural skin care products will eventually deteriorate. Chemical preservatives are generally used in the industry because they are much cheaper than, and extend the shelf life of the product more than, natural alternatives. The preferred preservative in the present disclosure is Biovert®, a product of Arch Chemicals®. Biovert® is a system of two linked preparations, which by themselves do not offer anti-microbial efficacy, but together offer anti-microbial efficacy. Biovert® mimics a naturally occurring antimicrobial-antioxidant protection system. When the two-part system is combined, a cascade of linked reactions takes place to generate antimicrobial products in situ. The cascade is initiated by the action of the glucose oxidase enzyme in the presence of its substrate (glucose) and oxygen. This generates $H_2O_2$, which is used by the lactoperoxidase to catalyze the oxidation of $I^-$ and $SCN^-$ anions, forming hypoiodite and hypothiocyanate which have antimicrobial activity.

The result is rapid microbial cell death. Other natural preservatives include tea tree and thyme essential oils, grapefruit seed extract, and D-alpha Tocopherol Acetate (Vitamin E).

The composition of the present invention may be used as a replacement for petroleum jelly or as a base for other products for application to the skin including SPF products. It is suitable for use in any petroleum jelly-based product and may be substituted for the petroleum jelly base in the product. It may also be used as a replacement for petroleum jelly in lubricants, anti-corrosion products, and for any other conventional uses known for petroleum jelly.

Examples of the base compositions and method of making such for the present invention are provided hereafter along with an example of a skin care product utilizing the composition of the present invention as a base. These examples are illustrative only and are not intended to be limiting.

EXAMPLES

Example 1

In a base of vegetable glycerine (e.g. 1000 ml.) after heating the glycerine to 70 dgrees centigrade and stirring, add at least 7.5% cetearyl glucoside (such as TEGO CARE® CG 90 from Evonik). Continue stirring and/or homogenize (by any means) until the cetearyl glucoside completely disappears (becomes transparent) in the glycerine base. Then let cool to room temperature, which will cause gelation, and to prevent oxidation, cover or seal in an appropriate container. The addition of vitamin E and waxes to stabilize and prevent oxidation of the resulting oil-free jelly is optional. Addition should occur while the solution is still hot and mixing is ongoing. Addition of all the other constituents listed above may be added as required and specified by the user. Oils may be optionally added as well.

Example 2

This example relates to the use of the oil-free jelly base to be used in products such as that outlined in Example 1. In this example, the jelly serves as one of two phases (Phase B) that are mixed together in a homogeneous manner to create an SPF product, moisturizer, cosmetic, etc. The resultant product can be a lip balm, cream, lotion or spray depending on the viscosity and constituents of Phase A. For example, Phase A is comprised of the following weight percent of constituents; arginine added and dissolved in water (5%) to which phosphatidyl choline is added (2%) with aloe vera gel (2%), and then subsequent mixing with glycerine (83%). Next, carrot oil (3%), jojoba oil (2%), olive oil (2%), as well as orange wax and beeswax (2%) with sodium borate (0.5%) are mixed all at 70 degrees centigrade to ensure homogeneity. Phase A can then accept a zinc oxide dispersion—Phase C in this case—(dispersed in glycerine or any suitable Ecocert® approved emulsifier) of up to 50 weight percent which will impart SPF properties. It is preferable to mix Phase A and Phase B together at a ration of 10-30:90-70 weight percent before adding Phase C. Mixing Phase A and B at various ratios will result in varying viscosities of the final solution (product). One of the resulting solutions has the consistency of a creamy off-white colored lotion which may or may not include the zinc oxide dispersion required to impart SPF properties.

Example 3

In a base of vegetable glycerine (e.g. 1000 mL) after heating the glycerine to 70 degrees centigrade and stirring, add at least 12 weight percent cetearyl glucoside (such as TEGO CARE® CG 90 from Evonik). Continue stirring and agitating purposely allowing for air or inert gases (which could be bubbled in during stirring) to enter the vessel until the cetearyl glucoside completely disappears (becomes transparent) in the glycerine base. Prior to cooling, an additional 5-15 weight percent of either talc or starch such as corn or arrowroot may also be added. The resultant solution is then allowed to cool to room temperature, which will cause gelation, and to prevent oxidation, cover or seal in an appropriate container. The gelled product will include a significantly greater amount of air or gas and therefore exhibits a much lower overall density than that of resulting product of Example 1 . Additionally, the resultant product is "fluffy" and therefore also less "sticky" when applied to the skin. The addition of vitamin E and waxes to stabilize and prevent oxidation of the resulting oil-free jelly is optional. Addition should occur while the solution is still hot and mixing is ongoing. Addition of all the other constituents listed above may be added as required and specified by the user. Oils may be optionally added as well.

In addition, the oil-free jellies described and comprised of glycerine and cetearyl glucoside, or any of the other edible emulsifiers, are themselves edible (in that the active ingredients are FDA food grade ingredients).

The above-described embodiments of the present invention are meant to be illustrative of preferred embodiments of the present invention and are not intended to limit the scope of the present invention. Various modifications, which would be readily apparent to one skilled in the art, are intended to be within the scope of the present invention. The only limitations to the scope of the present invention are set out in the following appended claims.

We claim:

1. A glycerine based jelly oil-free composition comprising; vegetable derived glycerine and an emulsifier, wherein said emulsifier is any known and /or commercially available glucoside containing emulsifier that also comprises temperature stabilizers and stiffening agents wherein said composition is a carrier for food and/or pharmaceutical grade products wherein said jelly comprises at least 80 percent by weight of glycerine and said emulsifier comprises no more than 20 percent by weight of said jelly composition, and wherein said jelly further comprises a combination of additives selected from the group consisting of clays, polymers, starches, salts, metal oxides, and lubrication enhancers.

2. The jelly composition of claim 1, wherein said combination of additives impart anti-corrosivity to said food and/or pharmaceutical grade products.

3. The jelly composition of claim 1, wherein said lubrication enhancers are selected from the group consisting of waxes and inorganic fillers.

4. The jelly composition of claim 1, wherein said combination of additives impart physio-mechanical strength and improved handling to said food and/or pharmaceutical grade products.

5. The jelly composition of claim 1, wherein said composition also includes a higher melting point than petroleum jelly.

6. The jelly composition of claim 4, wherein said composition is in contact with said food and/or pharmaceutical grade products.

7. The jelly composition of claim 1, wherein said emulsifier is a phospholipid.

8. The jelly composition of claim 1, wherein said emulsifier is a phospholipid and a glucoside.

9. The jelly composition of claim 1, wherein said emulsifier is a phosphatidyl choline.

10. The jelly composition of claim 1, wherein said jelly is a foamed gel composition wherein the foamed portion of said jelly is an amount such that said foamed gel is formed according to the weight percentage of singularly or a combination of either air or an inert gas added to said jelly to create said foamed gel composition.

11. The jelly composition of claim 1, wherein said jelly wherein said jelly further contains an additive selected from the group consisting of: vitamin E, additional vitamins and provitamins, aloe vera gel or aloe vera juice, bees wax, orange wax, and carnauba wax wherein said vitamin E, additional vitamins and provitamins, aloe vera gel or aloe vera juice, bees wax, orange wax, and carnauba wax are present in quantities that impart stiffness to said jelly.

12. A method for making a glycerine based oil-free jelly composition according to claim 1, comprising heating said glycerine to about 70 degrees Centigrade; mixing said glycerine with said emulsifier until said emulsifier is no longer visible in the mixed solution; and cooling said mixed solution to room temperature wherein said mixed solution congeals, thereby providing said jelly composition.

* * * * *